United States Patent

Bullat et al.

[11] Patent Number: 5,925,370
[45] Date of Patent: Jul. 20, 1999

[54] BIOREPELLENT MATRIX COATING

[75] Inventors: David M. Bullat, Carlsbad, Calif.;
Niraj Vasishtha, San Antonio, Tex.

[73] Assignee: The United States of America as represented by the Secretary of the Navy, Washington, D.C.

[21] Appl. No.: 08/985,430

[22] Filed: Dec. 4, 1997

[51] Int. Cl.⁶ .................................................. A01N 25/28
[52] U.S. Cl. .................... 424/408; 424/405; 424/406; 424/407; 424/419; 424/420; 424/195.1; 424/DIG. 10; 514/649
[58] Field of Search .......................... 523/122; 424/403, 424/405, 406, 407, 408–420, 195.1; 514/649

[56] References Cited

U.S. PATENT DOCUMENTS

| | | | |
|---|---|---|---|
| 5,322,862 | 6/1994 | Kurata et al. | 523/122 |
| 5,698,209 | 12/1997 | Shono et al. | 424/405 |

FOREIGN PATENT DOCUMENTS 9000005  1/1990  WIPO.

*Primary Examiner*—Neil S. Levy
*Attorney, Agent, or Firm*—Harvey Fendelman; Peter A. Lipovsky; Michael A. Kagan

[57] ABSTRACT

A biorepellent matrix structure comprises a resin and first and second microcapsules suspended in the resin. The first and second microcapsules each includes a first shell and a second shell, respectively, containing a biorepellent material that is released upon penetration of any of the first and second shells, as for example, by a biological organism. The biorepellent material, such as capsaicin, diffuses through the first and second shells at different rates. The different diffusion rates of the biorepellent material together provide a biorepellant matrix structure that exhibits long term protection against the formation of biological organisms that would otherwise accumulate on the matrix structure, and deters organisms from gnawing or chewing the matrix structure.

7 Claims, 3 Drawing Sheets

BIOREPELLENT MATRIX COATING

BACKGROUND OF THE INVENTION

The present invention generally relates to the field of biorepellent coatings, and more particularly, to a biorepellent coating matrix comprised of microcapsules containing capsaicin suspended in a resinous binder.

Biorepellent coatings are used to prevent or at least diminish the effects of mildew, fungus, and other biological organisms on structures such as the hulls of ships, cables, and buildings. One type of biorepellent coatings generally includes a biorepellent chemical such as capsaicin which has been mixed in a substrate material such paint. One problem with this type of coating is that the biorepellent efficacy of the coating tends to diminish rapidly as the biorepellent chemical diffuses through the substrate. Coatings of this type are described in U.S. Pat. No. 5,397,385, "Anti-Fouling Coating Composition Containing Capsaicin."

U.S. Pat. No. 5,322,862, "Resin Molding Composition For Preventing Gnawing Damage By Animals," describes a process for manufacturing microcapsules filled with capsaicin compound. However, the capsaicin diffuses through the microcapsules at a rate, which over time, lessens the repellent effect of coating materials embodying such microcapsules. Alternatively, such microcapsules may not provide sufficient minimum bioresistance to prevent organisms from forming on the composition.

A need, therefore exists, for a biorepellent coating that provides sufficient biorepellence to prevent or inhibit the formation of biological organisms over a predetermined period of time, while simultaneously providing sufficient biorepellent potency to discourage gnaws or bites from animals.

SUMMARY OF THE INVENTION

The present invention provides a biorepellent matrix structure that comprises a resin and first and second microcapsules suspended in the resin. The first and second microcapsules each includes a first shell and a second shell, respectively, containing a biorepellent material that is released upon penetration of any of the shells, as for example, by a biological organism. The biorepellent material such as capsaicin oil diffuses through the first and second shells at different rates. The different diffusion rates of the biorepellent material together provide a biorepellent matrix structure that exhibits long term protection against the formation of biological organisms that would otherwise accumulate on the matrix structure, and deter organisms from gnawing or chewing the matrix structure.

BRIEF DESCRIPTION OF THE DRAWINGS

Throughout the several view, like elements are referenced using like references.

DESCRIPTION OF THE PREFERRED EMBODIMENT

Figure 1:
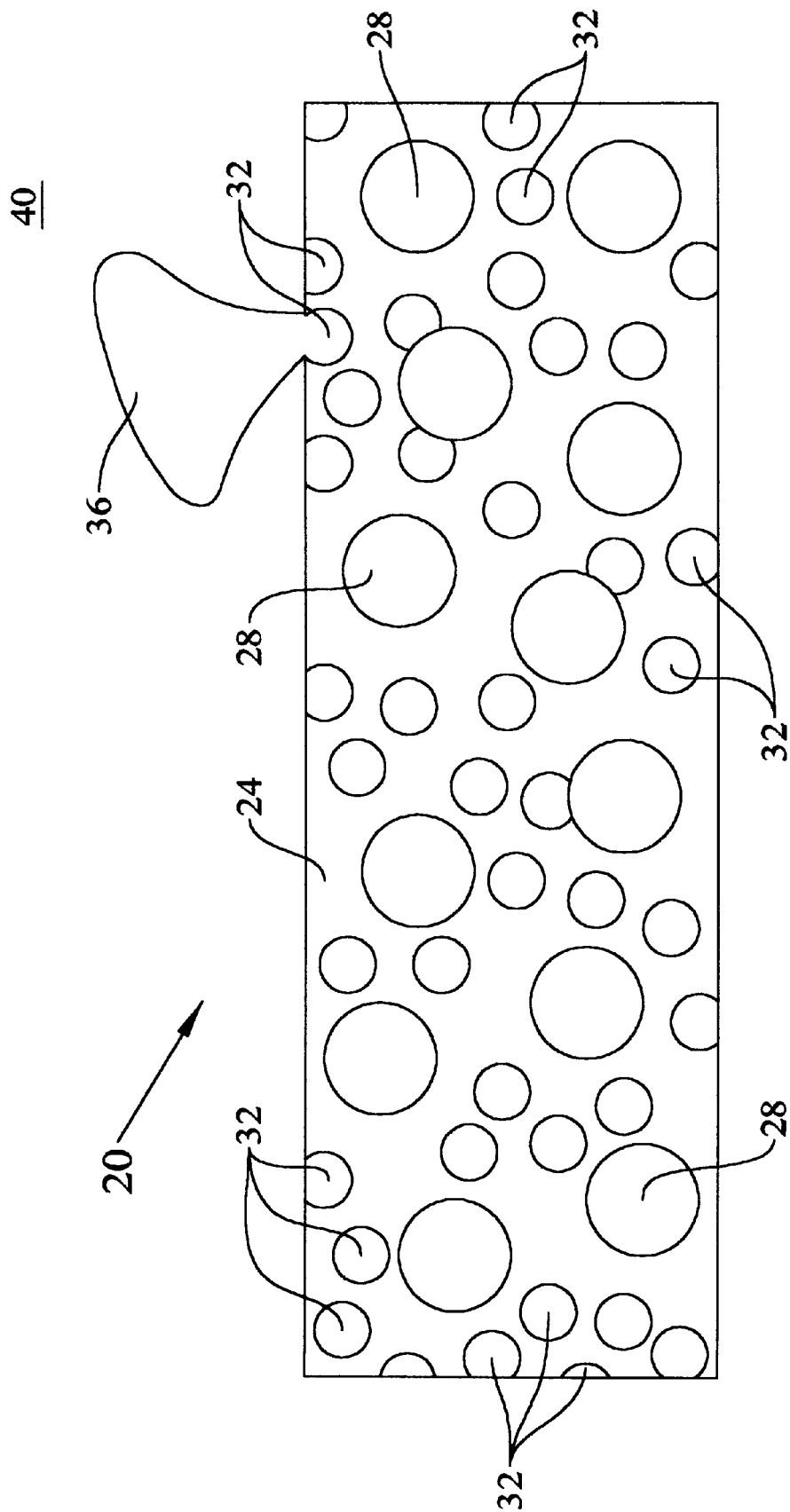
FIG. 1 is a cross-sectional view of a biorepellent matrix structure having various features of the present invention.
Figure 2:
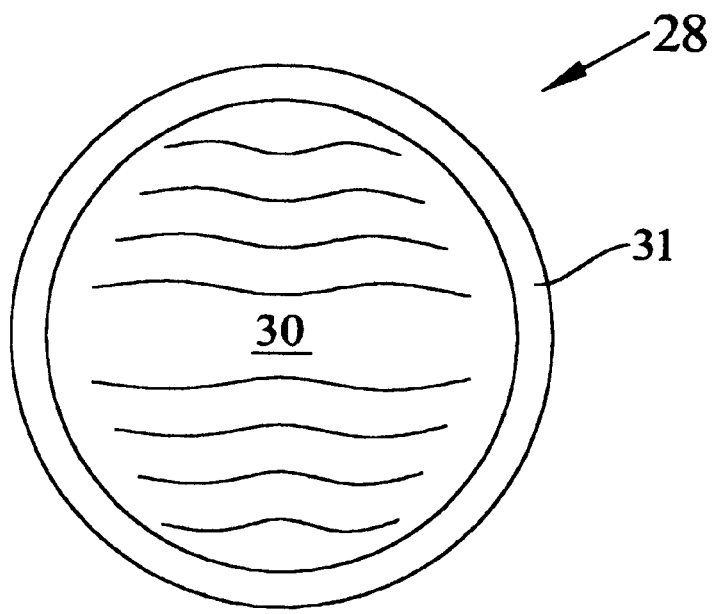
FIG. 2 is a cross-sectional view of a microcapsule used in the biorepellent matrix structure of FIG. 1.
Figure 3:
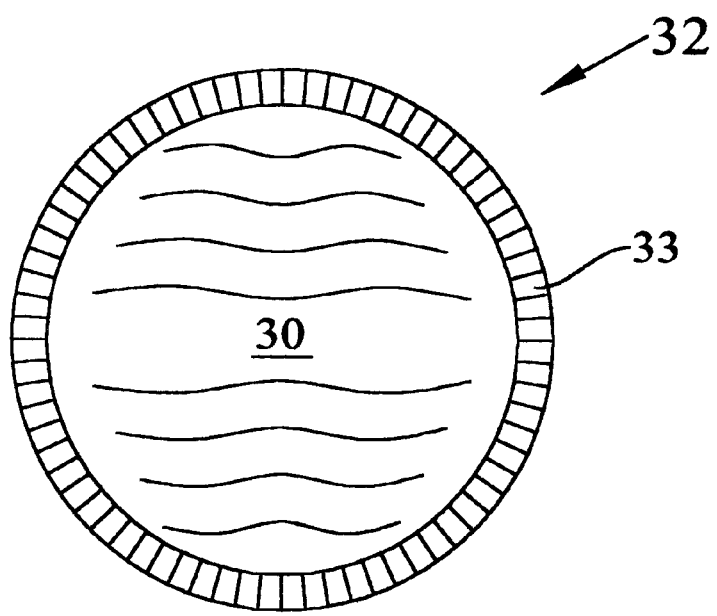
FIG. 3 is a cross-sectional view of another microcapsule used in the biorepellent matrix structure of FIG. 1.

Referring to FIG. 1, there is shown a biorepellent matrix structure 20 that comprises a resin 24 and a first set of microcapsules 28 and a second set of microcapsules 32 suspended in the resin. The microcapsules 28 and 32 may have different volumes. For example, the diameters of microcapsules 28 and 32 may be in the range of 10–50 microns and 1–5 microns, respectively. Microcapsule 28 includes a generally spherical shell 31 which contains biorepellent core material 30, as shown in FIG. 2. Microcapsule 32 includes a generally spherical shell 33 containing biorepellent core material 30, as shown in FIG. 3. The biorepellent core material 30, such as capsaicin mixed with a filler oil, diffuses through the shells 31 and 33 of microcapsules 28 and 32, respectively, at different rates and is released into the surrounding environment upon penetration of the shells by, for example, organisms such as common rodents or marine borers. Microcapsules 28 and 32 in resin 24 of matrix structure 20 may be, generally uniformly dispersed in the resin 24 at densities in the ranges of about $10^6$ to $10^8$ spheres/cm$^3$, and $10^9$ to $10^{12}$ spheres/cm$^3$, respectively.

FIG. 1 illustrates the penetration of one of microcapsules 32 by an organism which results in a plume 36 of biorepellent core material 30 seeping, for example, from a microcapsule 32 into a surrounding aqueous environment 40. Biorepellent core material 30 is designed to diffuse through the shells 31 and 33 of microcapsules 28 and 32, respectively, at different rates above a minimum effective flux rate to prevent the accumulation of biological organisms on the matrix structure 20. The matrix structure 20 may be used as a coating on structures made of wood, metal, concrete, plastic, or other material. The encapsulation of capsaicin oil, such as Oleoresin™, in microcapsules is well known, and is described in detail in U.S. Pat. No. 5,322,862, incorporated herein by reference.

The smaller sized microcapsules 32 each include a generally spherically shaped shell 33, preferably consisting essentially of polymethymethacrylate (PMMA), have a diameter in the range of about 1–5 microns and a wall thickness, $t_1$ in the range of about 0.08 to 0.6 microns. The shell 33 contains biorepellent core material 30 preferably consisting essentially of capsaicin oil as an active ingredient and a "filler" oil such as linseed oil, as described further herein. The capsaicin component of biorepellent core material 30 preferably diffuses through shells 33 of microcapsules 32 at a controlled flux rate in the range of 0.5 to 5 micrograms/cm$^2$/day. The shells 33 may have sufficient volume to store enough core material 30 so that core material 30 diffuses through the shell 33 within the range of the desired flux rate over a predetermined period, say for example, between 2 to 7 years.

Microcapsules 32 containing core material 30 may be prepared by several conventional encapsulation techniques such as solvent evaporation, interfacial polymerization, coacervation, and in-situ evaporation. Other techniques such as spray drying, rotating disk, and atomization may also be used to prepare microcapsules having diameters in the range of about 10 to 50 microns. Due to its high heat index, capsaicin oil is preferably diluted by compatible and soluble oils such as linseed or mineral oil, depending on the coating system, for high encapsulation efficiency. Dilution of the capsaicin oil in "filler" oil is necessary when processes such as coacervation are used because the high heat index of the capsaicin oil will cause disintegration of the shells 31 and 33, particularly when made of gelatin. Premature disintegration of the shell walls 31 and 33 would have the undesirable effect of significantly reducing the shelf life and performance of the microcapsules 28 and 32. Typical concentrations of capsaicin oil in linseed oil comprising the core 30 may be in the range of 1 to 20 w/w %.

The larger sized microcapsules 28 each include a generally spherically shaped shell 31 consisting essentially of cross-linked gelatin which may be prepared using complex coacervation techniques. The larger shells 31 may have a diameter in the range of about 10–50 microns and a wall thickness, $t_2$, in the range of about 0.95 to 10 microns. Each shell 31 contains biorepellent core material 30 preferably consisting essentially of capsaicin oil as an active ingredient and a "filler" oil such as linseed oil. The capsaicin component of biorepellent core material 30 preferably diffuses through shells 31 of microcapsules 28 at a controlled flux rate which may be in the range of 0.5 to 10 micrograms/$cm^2$/day. The shells 31 may have sufficient volume to store enough core material 30 so that core material 30 diffuses through the shell 31 within the range of the desired flux rate over a predetermined period, say for example, between 2 to 7 years. which preferably is sustained over a predetermined period, such as two to seven years. Microcapsules 28 may be prepared by several methods, such as by those described above with reference to microcapsules 32, including solvent evaporation, interfacial polymerization, in-situ polymerization, and phase separation. These techniques may be used to produce generally spheroid microcapsules having diameters within the range of about 1 to 5 microns.

Figure 4:
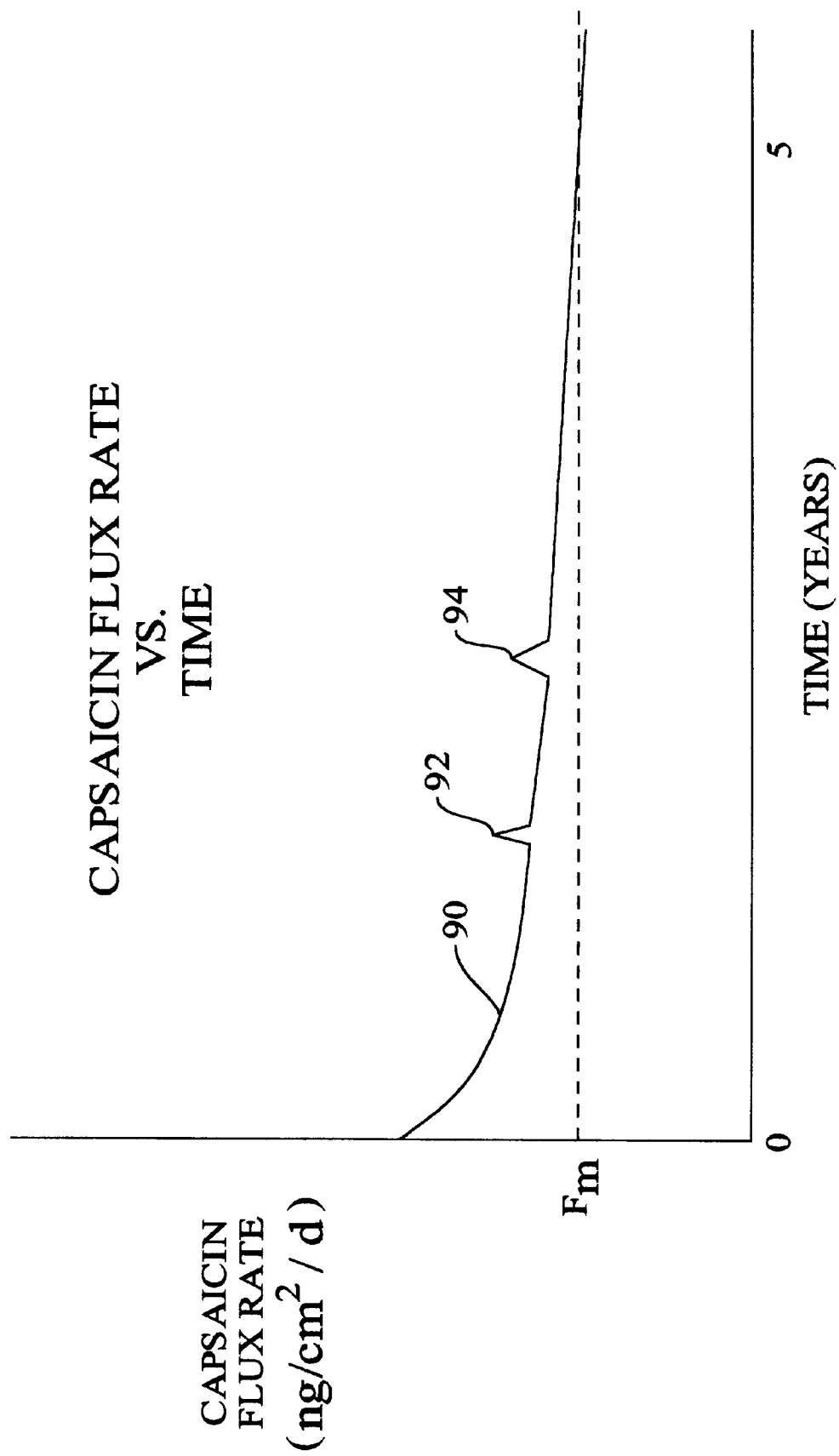
FIG. 4 is a graph illustrating the diffusion of a biorepellent substance from the matrix of FIG. 1.

FIG. 4 illustrates curve 90, representing one example of an expected functional relation between the flux of capsaicin oil from the biorepellent matrix structure 20 with respect to time. Curve 90 gradually decays so that the capsaicin oil flux through shells 31 and 33 of microcapsules 28 and 32, respectively, collectively exceeds the minimum effective flux rate $F_m$ required for a particular application, as for example, for a period which may be about 5 years. Peaks 92 and 94 in curve 90 represent the increased flux output of capsaicin oil resulting from perforation of any of two microcapsules 28 and/or 32 due to biting or gnawing by an animal.

Referring to FIG. 1, the resin 24 may be a polymer, such as alkyd, polyurethane, vinyl, or polyester, or may be selected from the group that includes epoxy and latex. The prepared microcapsules may be mixed with the resin 24 prior to the application stages. For example, with regard to vinyl based coating systems, the microcapsules 28 and 32 may be dispersed in the solvent which dissolves the vinyl polymer that is used as the vehicle for the resin 24. The typical concentration in which microcapsules 28 and 32 are added are in the range of about 1–5 w/w %, and 10–25 w/w %, respectively. Since the microcapsule shells 31 and 33 are immiscible in the solvent, the particle sizes are small, and their densities are comparable with that of the polymer solvent system. Simple agitation of the solvent and microcapsules 28 and 32 provides excellent dispersion of the microcapsules 28 and 32 within the resin 24.

Microcapsules 28 and 32 prepared using PMMA and nylon as shell materials in accordance with conventional encapsulation techniques such as solvent evaporation and interfacial polymerization, respectively, can be easily dispersed in resin 24 which may be made of a material from the group consisting essentially of alkyd polyurethane, polyester, epoxy, and latex coatings. Microcapsules 28 and 32 prepared by complex coacervation methods using gelatin as a shell material may be readily dispersed in vinyl-based coatings. In some applications, the addition of dispersion agents such as cationic, anionic, and/or non-ionic surfactants and filler oils may improve dispersion of the microcapsules 28 and/or 32 in the resin 24.

Obviously, many modifications and variations of the present invention are possible in light of the above teachings. It is therefore to be understood that within the scope of the appended claims, the invention may be practiced otherwise than as specifically described.

We claim:

1. A biorepellent matrix structure, comprising:
   a resin;
   first microcapsules suspended in said resin, each of said first microcapsules includes a first shell having a wall thickness in the range of about 0.08 to 0.6 microns, and contains capsaicin that is released upon penetration of said first shell, where said capsaicin diffuses through said first shell at about 0.5 to 5 micrograms/$cm^2$/day; and
   second microcapsules suspended in said resin, each of said second microcapsules includes a second shell having a wall thickness in the range of about 0.95 to 10 microns, and contains capsaicin that is released upon penetration of said second shell, where said capsaicin diffuses through said second shell at about 0.5 to 10 micrograms/$cm^2$/day.

2. The biorepellent matrix structure of claim 1 in which said resin is includes a polymer.

3. The biorepellent matrix structure of claim 1 in which said resin includes material selected from the group of polyurethane, vinyl, polyester, epoxy, and latex.

4. The biorepellent matrix structure of claim 1 wherein said first shell is made of a material that includes polymethylmethacrylate.

5. The biorepellent matrix structure of claim 1 wherein said second shell is made of a material that includes gelatin.

6. The biorepellent matrix structure of claim 1 wherein said first shell has a diameter in the range of about 1 to 5 microns.

7. The biorepellent matrix structure of claim 1 wherein said second shell has a diameter in the range of about 1 to 5 microns.

* * * * *